United States Patent [19]

Pesque et al.

[11] Patent Number: 5,669,385
[45] Date of Patent: Sep. 23, 1997

[54] ULTRASONIC SCANNING OF TISSUE MOTION IN THREE DIMENSIONS

[75] Inventors: Patrick René Pesque, Bothell; Gary Allen Schwartz; Jens Ulrich Quistgaard, both of Seattle, all of Wash.

[73] Assignee: Advanced Technology Laboratories, Inc., Bothell, Wash.

[21] Appl. No.: 615,125

[22] Filed: Mar. 13, 1996

[51] Int. Cl.⁶ .................................................. A61B 8/06
[52] U.S. Cl. ............................ 128/661.07; 128/916
[58] Field of Search ...................... 128/661.07–661.1, 128/916; 364/413.25

[56] References Cited

U.S. PATENT DOCUMENTS

| | | | |
|---|---|---|---|
| 5,197,477 | 3/1993 | Peterson et al. | 128/661.08 |
| 5,241,473 | 8/1993 | Ishihara et al. | 364/413.25 |
| 5,285,788 | 2/1994 | Arenson et al. | 128/660.05 |
| 5,329,929 | 7/1994 | Sato | 128/660.65 |
| 5,365,929 | 11/1994 | Peterson | 128/661.1 |
| 5,406,948 | 4/1995 | Skidmore | 128/661.1 |
| 5,471,990 | 12/1995 | Thirsk | 128/661.09 |
| 5,474,073 | 12/1995 | Schwartz et al. | 128/661.1 |
| 5,485,842 | 1/1996 | Quistgaard | 128/66.07 |
| 5,515,434 | 5/1996 | Iinama | 128/661.09 |

*Primary Examiner*—Francis Jaworski
*Attorney, Agent, or Firm*—W. Brinton Yorks, Jr.

[57] ABSTRACT

An ultrasonic diagnostic imaging system is provided which utilizes a multivariate processor to discriminate between Doppler power signals which were produced by moving tissue, and Doppler power signals which were produced by fluid flow. Discriminated moving tissue Doppler power signals are displayed in a three dimensional spatial presentation.

18 Claims, 8 Drawing Sheets

50%

50%

ULTRASONIC SCANNING OF TISSUE MOTION IN THREE DIMENSIONS

This invention relates to improvements in ultrasonic diagnostic imaging techniques, and in particular to ultrasonic scanning of tissue motion in three dimensions.

Ultrasonic diagnostic imaging systems can advantageously depict the motional characteristics of materials within the body through the Doppler phenomenon of sound waves. Color flow imaging has been developed which relies upon the phase or frequency shifts of received ultrasonic echoes to compute the direction and velocity of flowing blood and other fluids within the body. The estimations of these vectorial characteristics of fluid flow are correlated, or mapped, to specific colors or hues within a range of colors, then spatially presented in a two dimensional image along with a representation of the structure of the organs or vessels in which the flow is occurring, whereby the colors or hues indicate the direction and velocity of flow within the vessels or organs.

It is well known that Doppler signal echoes will be returned from any material in the body which is moving in relation to the ultrasonic transmitter, whether the material is a fluid or tissue. When the color flow ultrasound system is being adapted to depict fluid flow velocities, the echo information returned from tissue is generally suppressed by a frequency or amplitude sensitive filter known as a wall filter, leaving predominately fluid flow information for processing and display. An ultrasound system with such a configuration is shown in U.S. Pat. No. 5,197,477, for instance. Alternatively, a color flow ultrasound system can be adapted to depict the velocity of moving tissue by processing and displaying the echo information to which the wall filter is sensitive, to the exclusion of Doppler echo information characteristic of fluid flow. An ultrasound system with this configuration is shown in U.S. Pat. No. 5,285,788, for instance.

Following the development of color flow Doppler imaging a second technique for utilizing ultrasonic Doppler information began to be explored, which is known as power Doppler imaging. Power Doppler imaging does not attempt to estimate the velocity or direction of moving fluids or tissue. Instead, power Doppler imaging depicts the presence of motion by the intensity or power of the Doppler signal information. The power of the Doppler signal information may be mapped to a range of colors or hues for display, with the display thereby depicting, not the velocity or direction of motion, but the magnitude of the Doppler characteristic of the motion, by the color or hue in the display. Since, as mentioned above, Doppler echo signals emanate from both moving fluids and tissue, a power Doppler image can be formed representing both fluid flow Doppler power and tissue motion Doppler power.

It has recently been shown in U.S. Pat. No. 5,474,073 that power Doppler information can advantageously be displayed in three dimensional presentations. Three dimensional power Doppler imaging removes the uncertainty faced by the physician in trying to diagnose pathology existing in three dimensions from a series of confining two dimensional images. The physician is able to immediately see the volumetric completeness of a flow network in a three dimensional display. In addition, three dimensional power Doppler imaging of blood flow provides a second benefit, which is the segmentation of the three dimensional flow from structural clutter afforded by the motional characteristic of power Doppler information. Thus, the depiction of blood flow in a network of vessels can be distinctly and completely shown in a three dimensional power Doppler image without the need for any augmentation with B mode image information.

While the foregoing techniques present excellent three dimensional views of blood flow networks, it would also be desirable to view specific pathological conditions of organs such as the heart in three dimensions. In particular, it would be desirable to three dimensionally depict the moving heart valves and walls, and the effects of this motion of the walls of the organ on the capacity of chambers of the heart such as the left ventricle. It would further be desirable to more clearly define in three dimensions the boundaries of the beating heart such as the endocardium.

In accordance with the principles of the present invention, an ultrasonic diagnostic imaging system and imaging techniques are provided for three dimensional imaging of the beating heart and other moving vessels through power Doppler signal interpretation and display. A volume of the heart or other organ being examined is insonified with ultrasonic waves and the returning echo information is processed by a power Doppler processor to produce spatially oriented power Doppler information. A tissue motion detector differentiates power Doppler information returning from tissue from that which is returned by fluids. The spatially oriented power Doppler information returned from moving tissue is then processed and displayed in a three dimensional image presentation. The resulting images are clutter free, highly segmented depictions of the heart and other three dimensional moving organs and vessels.

Figure 1:
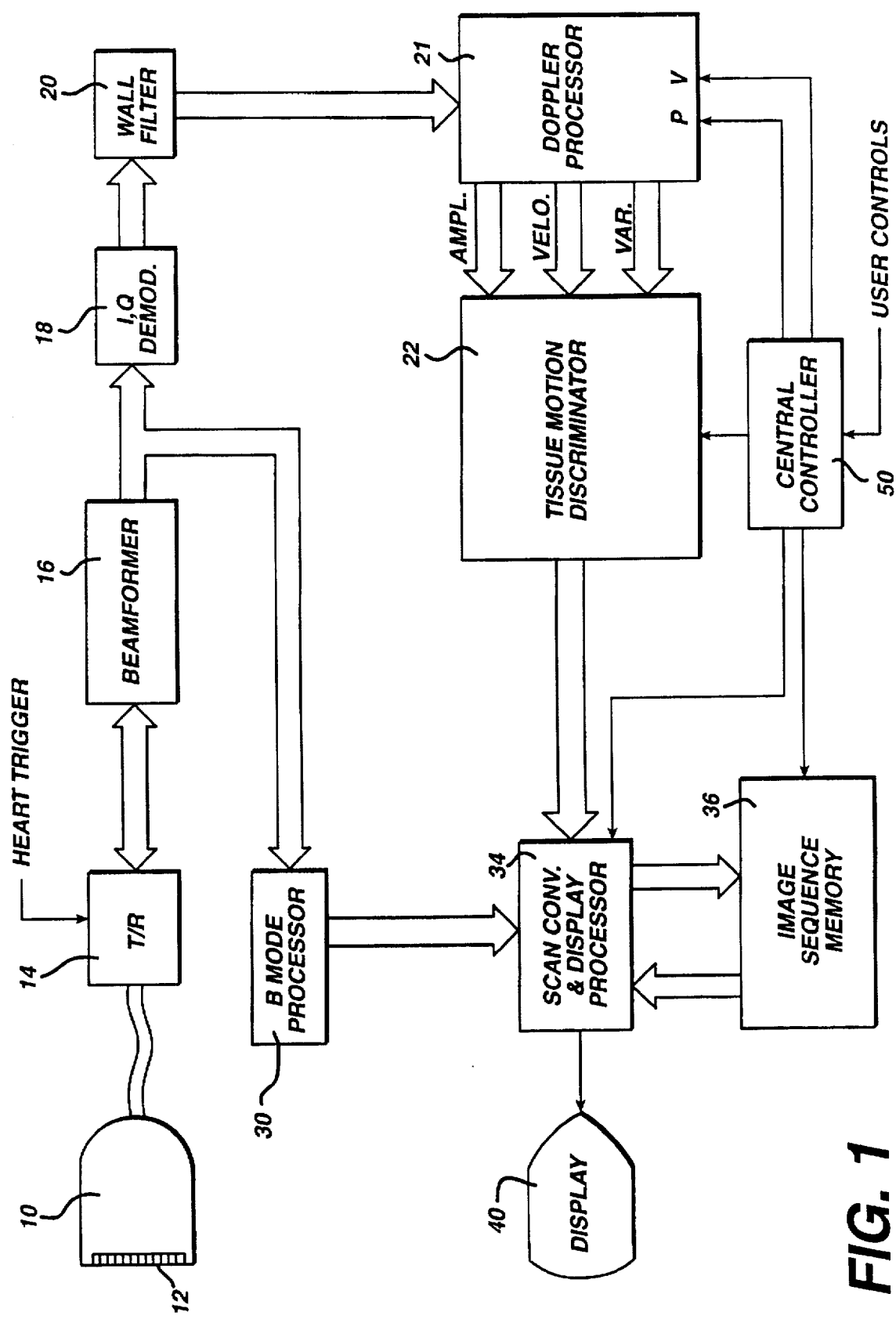
FIG. 1 illustrates in block diagram form an ultrasonic diagnostic imaging system constructed to operate in accordance with the principles of the present invention.

Referring first to FIG. 1, a block diagram of an ultrasonic diagnostic imaging system constructed in accordance with the principles of the present invention is shown. An ultrasonic probe 10 includes a multielement transducer 12 which transmits waves of ultrasonic energy into the body of a patient and receives ultrasonic echoes returning from structures in the body. In the case of ultrasonic wave transmission for Doppler interrogation of the body, it is the echoes returning from moving tissue, blood and other fluids in the body that are of interest. The ultrasonic probe 10 is connected to a transmitter/receiver 14 which alternately pulses individual elements of the transducer to shape and steer an ultrasonic beam, and receives, amplifies and digitizes echo signals received by the transducer elements following each pulse transmission.

Figure 2:
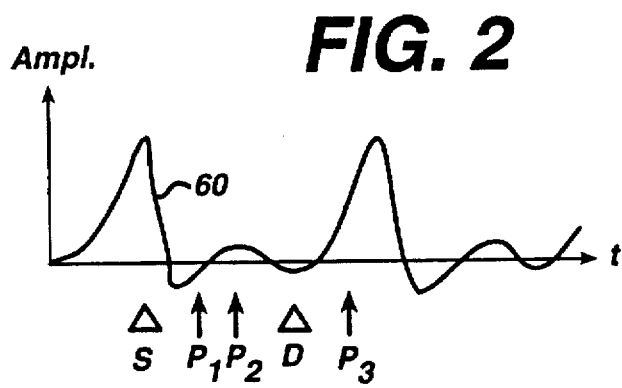
FIG. 2 illustrates the QRS waveform of a patient's heartbeat used to trigger image acquisition in the system of FIG. 1.

When the ultrasound system is used to acquire echo information from the beating heart, the needed information generally can not be acquired while the heart is substantially in one position during its cycle of contraction and expansion. To account for the motion of the heart, echo acquisition is acquired at the same phase or phases of the heart cycle over a number of heart cycles. FIG. 2 illustrates a heartbeat waveform 60 which may be produced by the EKG module of an ultrasound system. The waveform may also be derived from Doppler measurements of the cardiac system. FIG. 2 shows two triangular reference markers S and D, which indicate the waveform when the heart is at its peak systolic and peak diastolic phases. When the heart is at these phases of its cycle the heart is momentarily stationary as the heart muscle reverses from contraction to relaxation or vice versa. When tissue motion of the heart is being detected these phases are generally not imaged, but are useful as timing markers to reference the times or phases at which images are acquired. FIG. 2 shows three arrow markers $P_1$, $P_2$, and $P_3$ which the user may move in relation to the waveform 60 and the reference markers. Setting the arrow markers as shown in FIG. 2 will cause the ultrasound system to acquire echo information at the indicated phases of the heart cycle, and the heart trigger causes the transmitter/receiver 14 to transmit ultrasonic pulses at these phases of successive heart cycles until the necessary echo information has been received.

The transmitter/receiver 14 is coupled to a beamformer 16 which controls the times of activation of specific elements of the transducer 12 by the transmitter/receiver in concert with the heart trigger. This timing enables the transducer 12 to transmit a shaped and focused ultrasound beam in a desired direction at the desired heart phases. The beamformer 16 also receives the digitized echo signals produced by the transmitter/receiver during echo reception and appropriately delays and sums them to form coherent echo signals.

Figure 3:
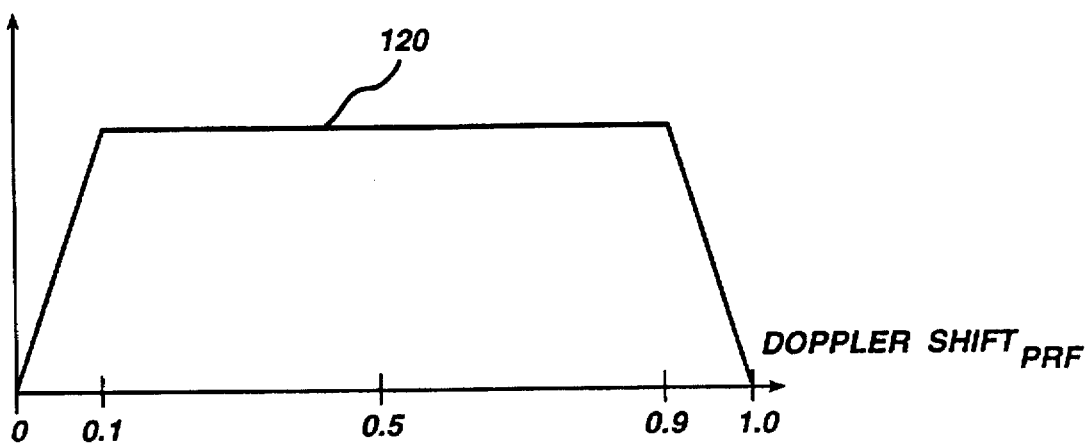
FIG. 3 illustrates the characteristics of the wall filter of the system of FIG. 1.

The echo signals produced by the beamformer 16 are coupled to a B mode processor 30 and to an I,Q demodulator 18. The B mode processor processes the amplitude information of the echo signals on a spatial basis for the formation of a structural image of the tissue in the area of the patient being scanned. The I,Q demodulator 18 demodulates the received echo signals into quadrature components for Doppler processing. The I,Q components are filtered by a wall filter 20 to eliminate stationary Doppler signals from the sequence of Doppler signals. To accomplish this, the wall filter is given a bandpass characteristic with a zero response at a zero velocity. A typical response characteristic 120 for the wall filter 20 is shown in FIG. 3, in relation to the Doppler shift frequency of the received signals. The abscissa of the characteristic is normalized to the pulse rate frequency (PRF) of Doppler transmission, that is, the abscissa is in units of the Doppler shift frequency divided by the PRF. As the characteristic 120 shows, the wall filter 20 has a zero response at a Doppler shift of zero, which rises to a maximum response at 0.1 of the normalized Doppler shift. At about a value of 1.9 the response rolls off to a response of zero at a Doppler shift of 2.0. The filtered I,Q components are then applied to a Doppler processor 21.

The Doppler processor 21 receives a number of Doppler signals from each sample volume in the volume being imaged and processes the signals to estimate Doppler values such as velocity, amplitude (power), and variance at each sample volume. Estimation of the Doppler velocity can be performed by auto correlation processing as described in U.S. Pat. No. 5,386,830 to determine the Doppler frequency at each sample volume. The Doppler processor 21 will also process the Doppler signals to estimate Doppler power at each sample volume location. The Doppler processor 21 can estimate the Doppler signal power magnitude from the I,Q signal components at each sample volume location using the expression $(I^2+Q^2)^{1/2}$. Alternatively, since quadrature signals are not necessary for Doppler power estimation, estimates of Doppler power can be produced from the I signal components alone. The Doppler power estimates at each sample volume location are, if desired, averaged with earlier acquired power estimates for each sample volume location. In a preferred embodiment, each sample volume location is interrogated by a number of pulses and the Doppler processor 21 utilizes the signals obtained from all interrogations in the estimations of Doppler power at the sample volume locations.

The sample volume Doppler values are then coupled to a tissue motion discriminator 22. The tissue motion discriminator 22 can be operated as simply a pass-through circuit to pass the Doppler power, velocity or variance values on to a scan converter and display processor, where they may be spatially mapped to a range of intensities or colors and displayed in conventional fashion with structural information from the B mode processor 30. Alternatively, the tissue motion discriminator can be operated in accordance with the principles of the present invention to identify Doppler signals resulting from tissue motion.

Figure 4:
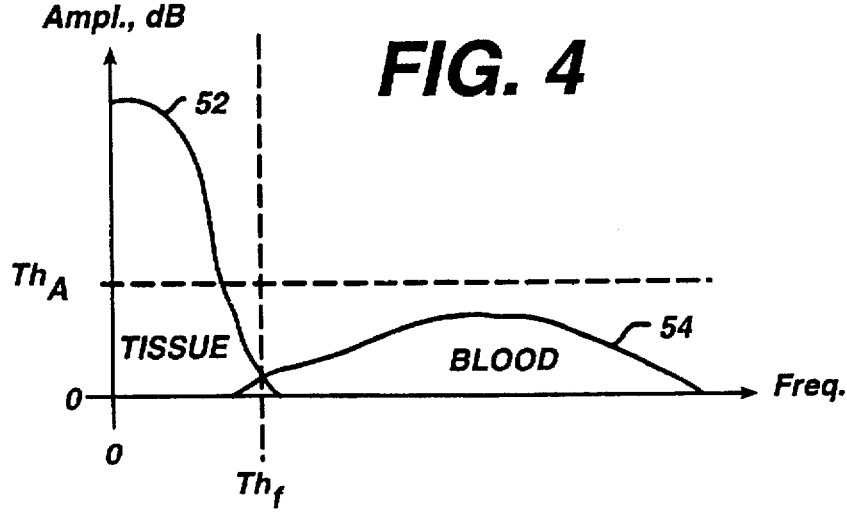
FIG. 4 illustrates techniques for differentiating between blood flow and tissue motion in accordance with the principles of the present invention.

In accordance with the principles of the present invention the Doppler system of FIG. 1 also includes a power Doppler imaging capability for both fluids and moving tissue. Heart tissue motion and blood flow Doppler values can be distinguished from each other in a number of ways. Referring to FIG. 4, a curve 52 delineates on a frequency and amplitude basis the Doppler components normally produced by moving tissue. A curve 54 delineates the Doppler components normally resulting from blood flow. As these two curves illustrate, the tissue components are normally low in frequency due to their characteristic low velocity of motion, and are also normally much greater in amplitude than the blood flow components.

Figure 5A:
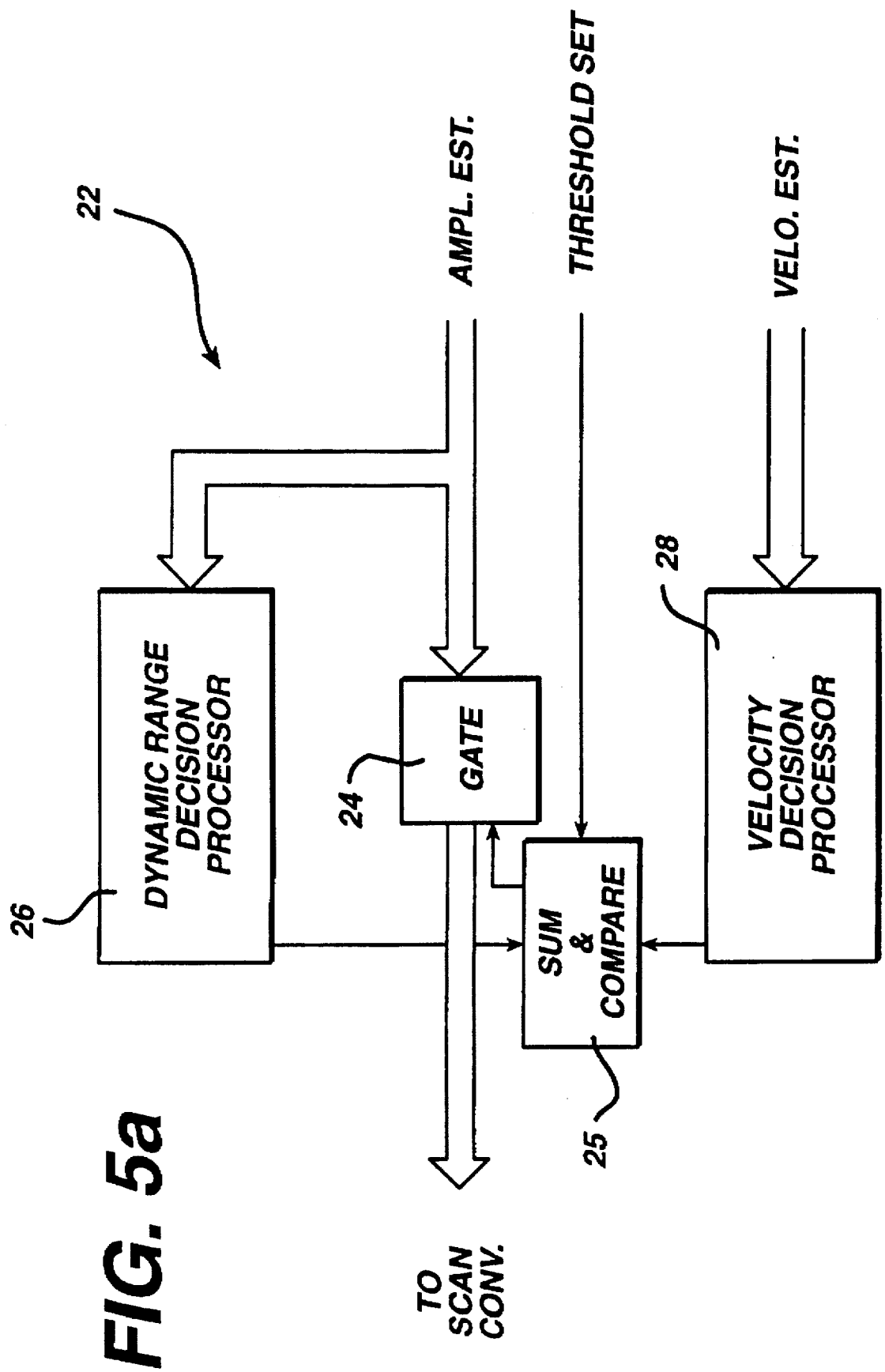
FIGS. 5a and 5b illustrate in block diagram form two embodiments of the tissue motion discriminator of FIG. 1.
Figure 6:
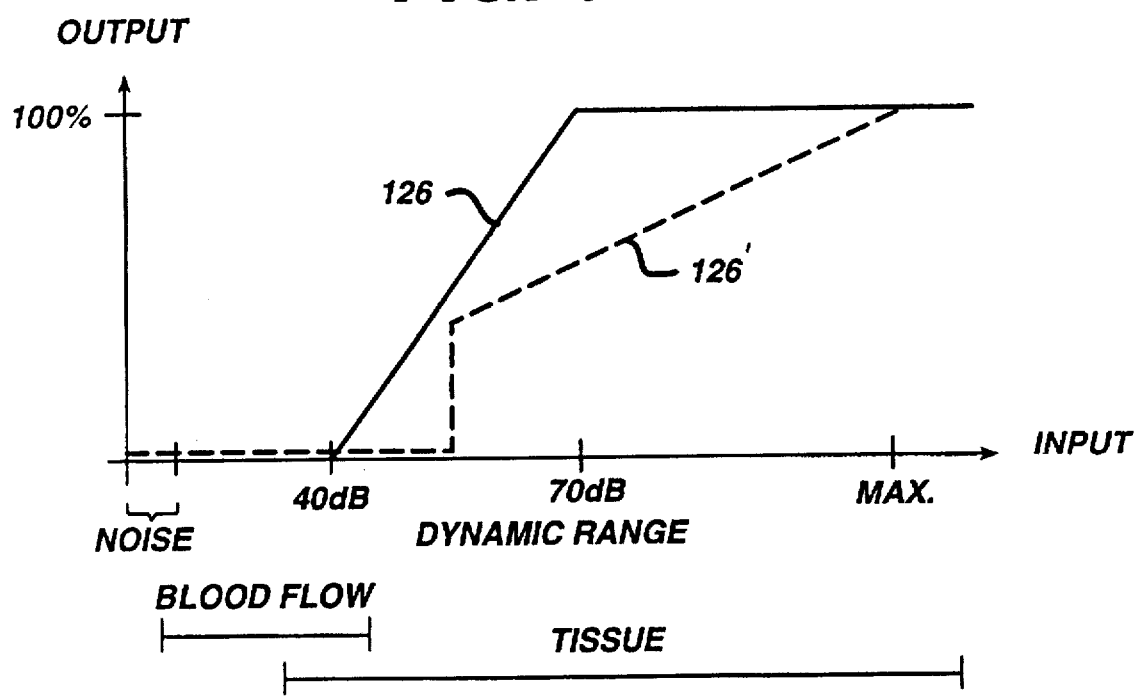
FIG. 6 illustrates the characteristics of the dynamic range decision processor of FIG. 5.
Figure 7:
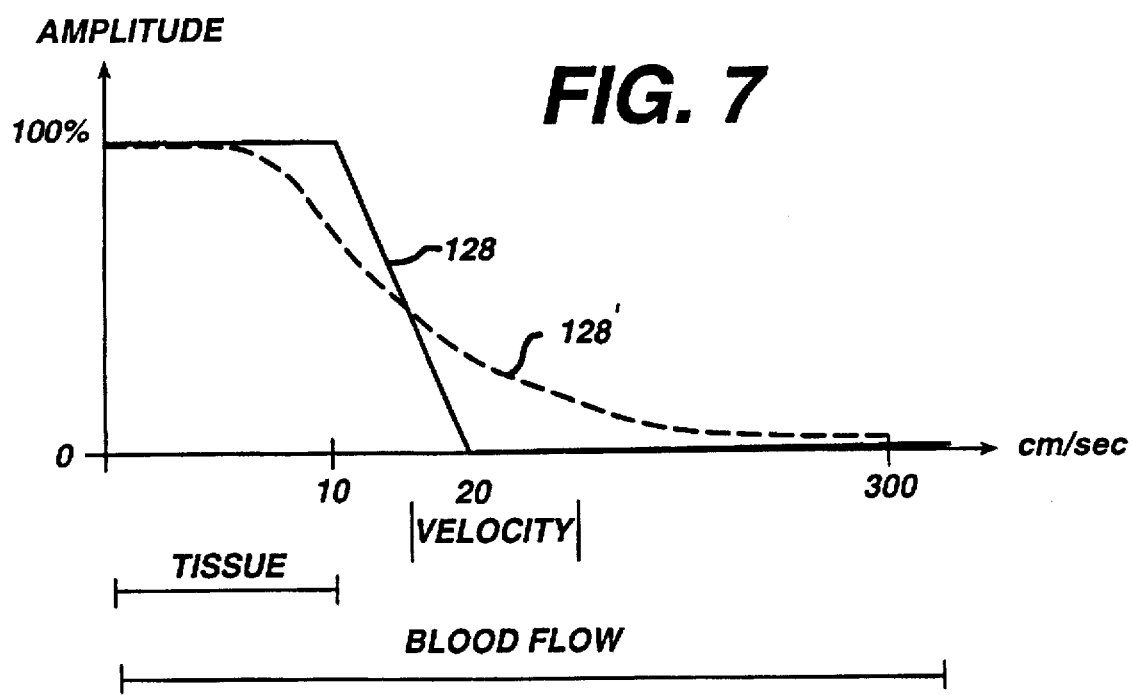
FIG. 7 illustrates the characteristics of the velocity decision processor of FIG. 5.

One technique for separating the moving tissue Doppler components from the blood flow components is shown in the detailed tissue motion discriminator block diagram of FIG. 5a, together with the response characteristics of FIGS. 6 and 7. In FIG. 5a a gate 24 selectively passes a Doppler power (amplitude) estimate to the scan converter and display processor depending upon the result of a multivariate analysis which examines both the amplitude (power) and velocity (frequency) of the Doppler signal. The amplitude information of the Doppler signal from a particular sample volume is applied to both the gate 24 and to a dynamic range decision processor 26. The dynamic range decision processor 26 can have a transfer function as illustrated by the curves in FIG. 6. The curve 126 is a response curve of linear segments by which an output is produced by the dynamic range decision processor 26 as a function of the input signal amplitude. The alternative response curve 126' is a more complex curve with a delayed, more discontinuous characteristic as compared with curve 126. In each case, very low amplitude signals are regarded as noise and produce no output, as do low amplitude signals up to approximately 40 dB, or higher in the case of curve 126'. The latter range is the range of amplitudes which may be expected for blood flow signals. Signals above an amplitude of around 40 dB are regarded as resulting from tissue motion. The curves undergo a transition between 40 dB and 70 dB, above which signals can be ruled with considerable confidence as resulting from tissue motion. Hence, the dynamic range decision processor 26 will produce an output signal which follows curve 126 or 126' as a function of the amplitude of the applied Doppler signal. The output signal of the dynamic range decision processor 26 is applied to a sum and compare circuit 25 in FIG. 5a.

At the same time, the Doppler velocity estimate for the same sample volume is applied to a velocity decision processor 28. The velocity decision processor 28 responds to the velocity value to produce an output signal which follows one of the transfer function curves 128 or 128' of FIG. 7. As the curves 128 and 128' show, signals with a velocity (or equivalent frequency) from zero to ten centimeters per second can result from either moving tissue or blood flow. Doppler velocities above the velocity of about 20 cm/sec most likely will have resulted from blood flow since tissue will not generally exhibit these higher velocities. Hence the curves 128 and 128' undergo transition between ten and twenty cm/sec until reaching a zero output level. Thus, the velocity decision processor 28 will produce an output signal which follows curve 128 or 128' as a function of the velocity of the applied Doppler signal. The output signal of the velocity decision processor 28 is also applied to the sum and compare circuit 25.

The two decision processor output signals are summed by the sum and compare circuit 25 and the sum compared against a threshold which the user may set. This threshold is applied to the sum and compare circuit 25 as shown by the "threshold set" line. If both decision signals are at their "high" levels the Doppler signal has been judged to result from moving tissue by both processors and hence the power Doppler signal will be gated to the scan converter and display processor 34. If both decision signals are at their "low" levels the Doppler signal has been judged to result from blood flow by both processors and no signal will be gated to the scan converter and display processor 34. For signals in the transition regions between the high and low levels of the decision circuit outputs, the combined decision signals will be either above or below the threshold set by the user. Thus, the threshold setting enables the user to tip the decision as to whether Doppler signals resulting in these transitional characteristics are judged to have resulted from blood flow or moving tissue. This multivariate process of analyzing signals by both their amplitude and frequency characteristics results in a better discrimination of blood flow and moving tissue Doppler signals.

Figure 5B:
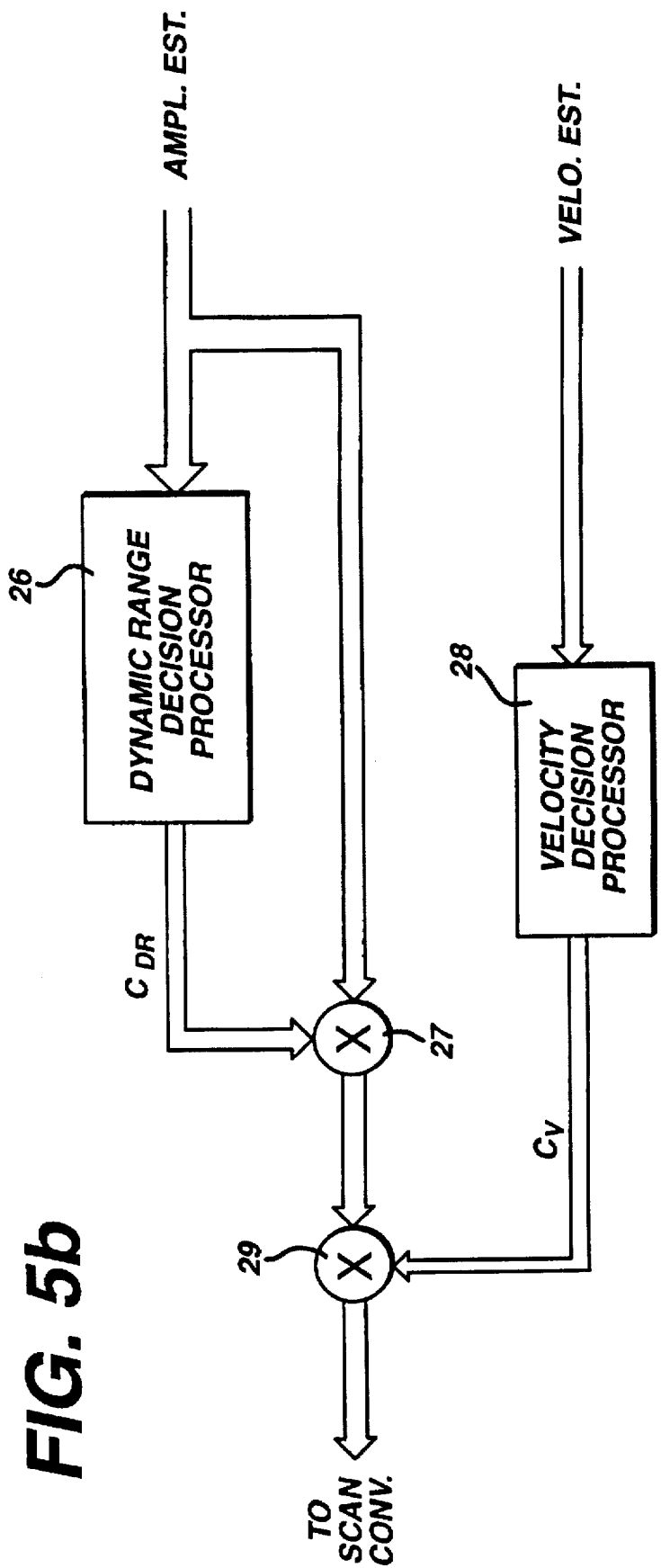

An alternative system for discriminating Doppler signals resulting from tissue motion is shown in FIG. 5b. This alternative system operates by weighting Doppler amplitude estimates by coefficients determined by the dynamic range and velocity decision processors. In FIG. 5b the Doppler amplitude estimates are applied to the dynamic range decision processor 26 which produces a coefficient $C_{DR}$ between zero and one (where "one" is at the 100% level in FIG. 6) in accordance with the transfer characteristic curve of the processor. The Doppler amplitude value is then multiplied by the coefficient $C_{DR}$ by a multiplier 27. The Doppler velocity estimate for the same sample volume is applied to the velocity decision processor 28 which similarly produces a coefficient $C_V$ between zero and one (where "one" is at the 100% level in FIG. 7) in accordance with the transfer characteristic curve of the velocity decision processor. The weighted value resulting from the product of the Doppler amplitude value and the $C_{DR}$ coefficient is multiplied by the second coefficient $C_V$ by a multiplier 29 to produce a final Doppler amplitude value weighted by coefficients by both processors. This identified tissue motion value is applied to the scan converter of FIG. 1.

The Doppler power estimates which have been identified by one of the above processes as resulting from moving tissue are coupled along with their spatial coordinates to the scan converter and display processor 34 which spatially arranges the Doppler power display values in the desired image format, e.g., sector or rectangular. The resulting images may be immediately displayed in a real time image sequence on a display 40 or may be stored as separate planar images in an image sequence memory 36. The two dimensional Doppler power tissue images may be recalled from the image sequence memory 36 for three dimensional processing as discussed below.

User operation of the system of FIG. 1 is effected through various user controls coupled to the central controller 50 which enable the user to select the type of imaging to be performed, i.e., B mode, color velocity Doppler or Doppler power imaging; the threshold levels against which the decision processor results are compared; and to store and retrieve images from the image sequence memory 36 for three dimensional display, for example.

Figure 8:
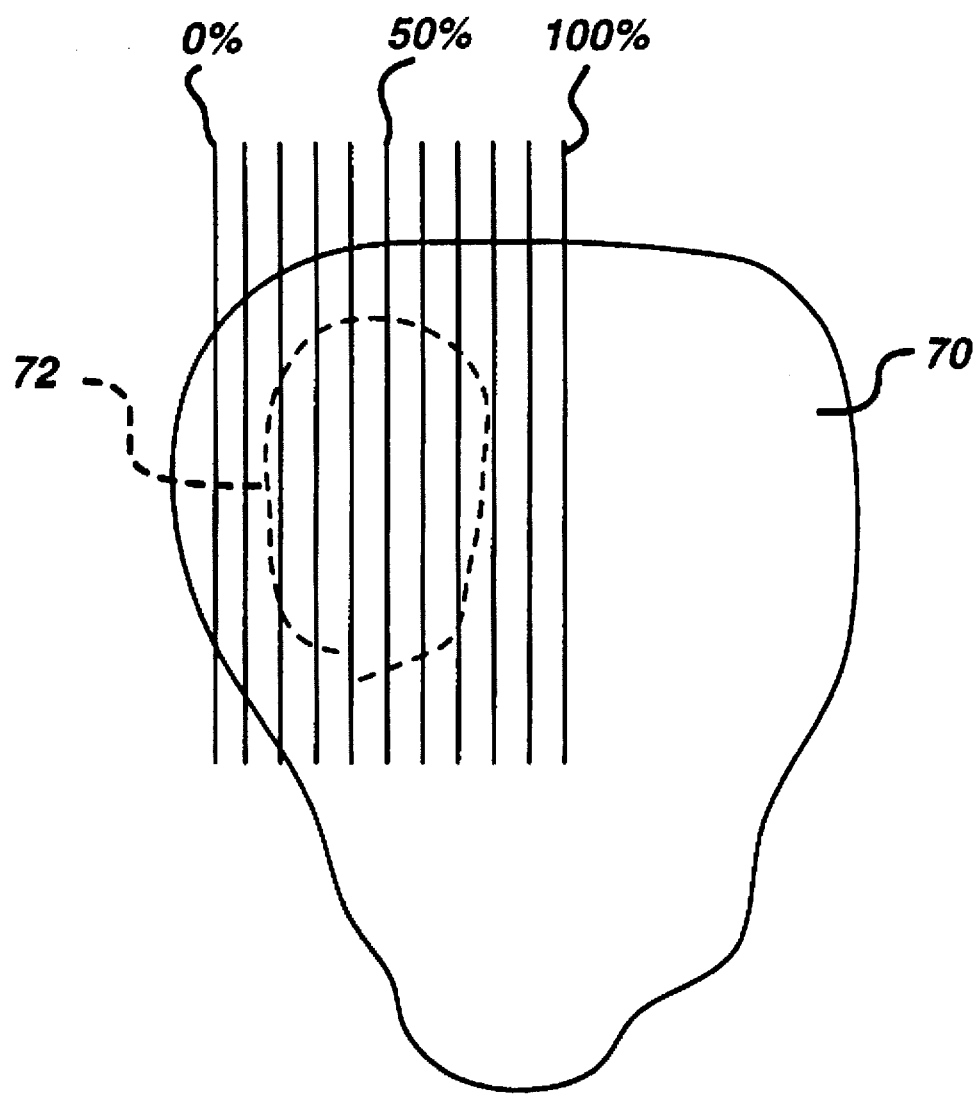
FIG. 8 illustrates the acquisition of image planes of the heart for three dimensional display in accordance with the principles of the present invention.

FIG. 8 illustrates a technique for forming three dimensional power Doppler images of the heart in accordance with the principles of the present invention. An outline of the heart 70 is shown, which includes a dashed outline 72 of the left ventricle, which is to be imaged in this example. The ultrasonic probe 10 is moved across the chest above the heart, acquiring a number of image planes shown edge-on from the rear of the heart in FIG. 2 and labeled from 0% to 100% for reasons which will be discussed below. As the probe 10 is slowly moved from left to right in the example of FIG. 2 the transducer 12 is actuated each time the heart is in one of the desired phases ($P_1$, $P_2$, or $P_3$, for example) of its beating cycle as determined by the heart trigger pulses applied to the transmitter/receiver 14. The probe can be moved freehand as described in U.S. Pat. No. 5,474,073 or can be moved by a three dimensional scanning device as described in U.S. Pat. No. 5,487,388. The spacing between image planes can be estimated as described in U.S. Pat. No. 5,474,073, or the respective planar positions can be measured and recorded using the scanning device or a device internal to the probe as described in U.S. Pat. Nos. 5,353,354 or 5,127,409. At the conclusion of scanning a series of spatially separate planar Doppler power images of moving tissue has been acquired for each indicated phase of the heart cycle.

Figure 9:
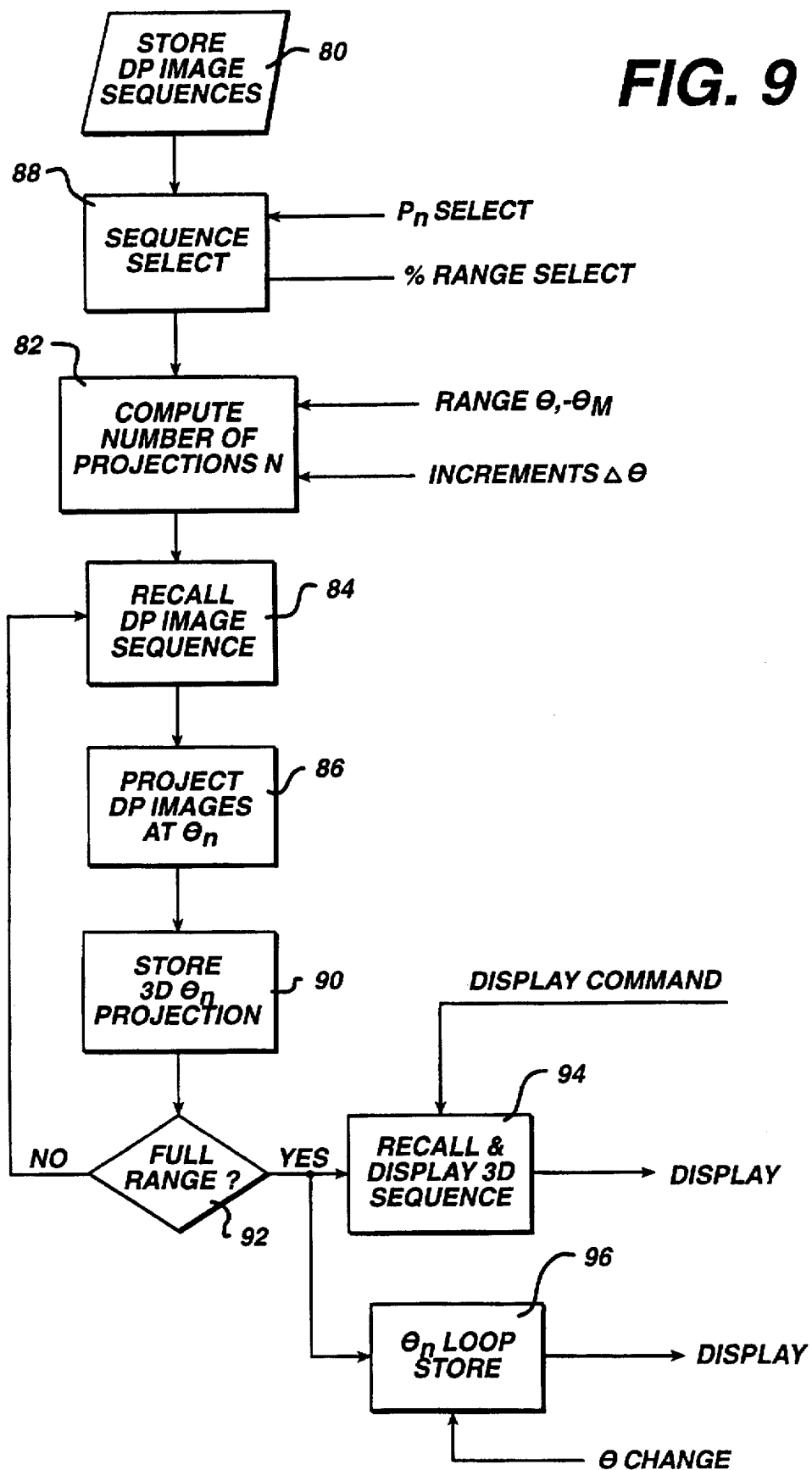
FIG. 9 is a flowchart of three dimensional processing of the image plane information acquired in accordance with FIG. 8.

After this sequence (or sequences) of Doppler power images of the left ventricle has been acquired each sequence is stored in the image sequence memory 36. The sequence is then processed into a three dimensional display as illustrated by the flowchart of FIG. 9. In step 88 the user selects the heart phase for which a three dimensional display is desired, using for instance one of the P markers shown in FIG. 2. The sequence of images acquired from this phase of the heart cycle is then processed for three dimensional display. In step 82 the process receives processing parameters provided by the user controls. One parameter is the range of viewing angles, $\theta_1 - \theta_M$, over which the three dimensional presentation is to be viewed. The other parameter is the increment $\Delta\theta$ between each viewing angle in the range. For instance the user could input a range of viewing angles of +60° to −60°, referenced to a line of view in a plane which is normal to the plane of the first image in the sequence, and a range increment of 1° as the viewing angle is changed. From these inputs the number of three dimensional projections needed is computed in step 82. For example, 121 projections are needed to display a 120° range span in one degree increments.

The process now begins to form the necessary sequence of 121 Doppler power image projections. In step 84 the planar Doppler power images of the selected heart phase are recalled from the image sequence memory for sequential processing by the scan converter and display processor 34. In step 86 each planar image is rotated to one of the viewing angles $\theta_n$, then projected back to the viewing plane. The pixels of the projected planar images may, if desired, be accumulated on a maximum intensity basis at this point in the process. Each projected planar image is overlaid over the previously accumulated projected images but in a transposed location in the image plane which is a function of the viewing angle and the interplane spacing: the greater the viewing angle, the greater the transposition displacement from one image to the next. The display pixels chosen from the accumulated images are the Doppler power pixels taken at each point in the image planes from all of the overlaid pixels accumulated at each point in the image. This effectively presents the left ventricle in a Doppler power representation as seen by the viewer along every viewing line between the viewer and the three dimensional image. In a preferred embodiment the relocation of image points after rotation about the y axis, projection and transportation may be expressed as:

$$\begin{bmatrix} x' \\ y' \end{bmatrix} = \begin{bmatrix} x\cos(\theta) \\ y \end{bmatrix} + \begin{bmatrix} z\sin(\theta) \\ 0 \end{bmatrix}$$

and the relocation of image points after rotation about the x axis, projection and transposition may be expressed as:

$$\begin{bmatrix} x' \\ y' \end{bmatrix} = \begin{bmatrix} x \\ y\cos(\theta) \end{bmatrix} - \begin{bmatrix} 0 \\ z\sin(\theta) \end{bmatrix}$$

where $\theta$ is the angle of rotation, (x, y, z) are the coordinates of a point to be relocated, and (x', y') are the coordinates of a point in the viewing plane after relocation.

After all of the planar images have been rotated, projected, transposed, overlaid, and the maximum intensities at each pixel chosen, the resulting three dimensional image for the viewing angle $\theta_n$ is stored in step 90 in the image sequence memory 36 as a brightness modulated monochrome image in a three dimensional image sequence. In step 92 the process returns to step 84 and proceeds through steps 84–92 until the full three dimensional image sequence has been stored in memory.

The stored three dimensional sequence is now available for recall and display in step 96 upon command of the user. As the sequence is recalled and displayed in real time, the user sees a three dimensional power Doppler presentation of the heart wall as it appears at a selected phase of the heart cycle. The volumetric region is viewed three dimensionally as if the user were moving around the heart and viewing the heart chamber from different viewing angles. The user has the impression of moving over a range of viewing angles $\theta_1$–$\theta_M$ around the left ventricle. The viewer can sweep back and forth through the sequence, giving the impression of moving in a semicircular path around the left ventricle in two directions.

Figure 10A:
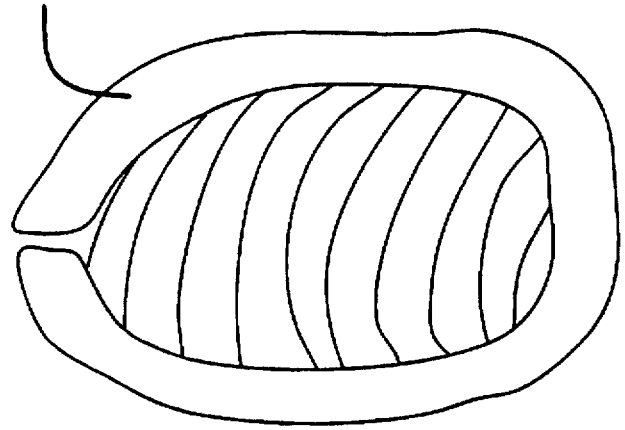
FIGS. 10a and 10b illustrate three dimensional power Doppler images of a chamber of the heart while in a relaxed phase of operation.
Figure 10B:
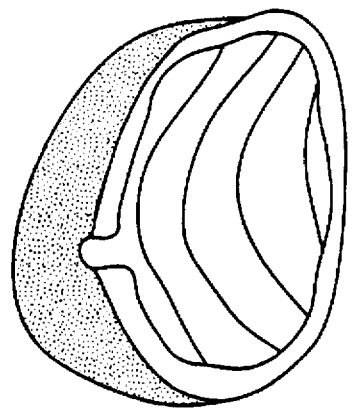
Figure 11A:
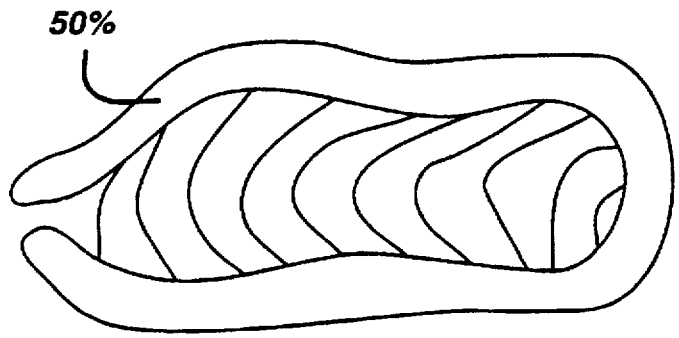
FIGS. 11a and 11b illustrate three dimensional power Doppler images of a chamber of the heart while in a contracted phase of operation.
Figure 11B:
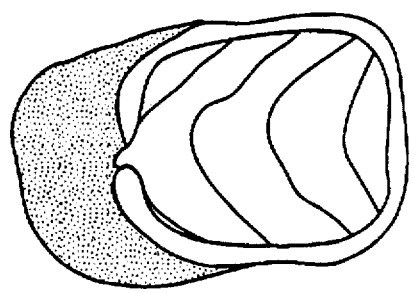

Since the clinician is usually interested in examining the inner wall of the heart chambers and not their outer dimensions, it may be desirable to view a chamber of the heart in three dimensional cross section. For example, the left side of the left ventricle can be processed and displayed using the planar images from 0% to 50% in FIG. 8. FIG. 10a is a view looking into the left side of the left ventricle when the heart is almost fully relaxed as it might be at phase $P_2$, where the nearest cross sectional plane to the viewer is the 50% plane of FIG. 8. Near peak systole when the heart is contracted, as it might be at phase $P_3$, the same view appears as shown in FIG. 11a. These views, and the views of the same section of the left ventricle when rotated as shown in FIGS. 10b and 11b, are obtained by selecting only a certain range of planar frames for three dimensional processing in step 88. In this way the clinician may examine the endocardium by first creating then rotating and inspecting a three dimensional image of one half of the heart chamber (planes from 0% through 50%), then repeating the process of the other half of the heart chamber (for planes 50% through 100%).

For a fully real time three dimensional display a number of loops of three dimensional images are processed and stored in a $\theta_n$ loop store 96, then recalled and displayed each time a different viewing angle $\theta$ is selected. Each loop is a sequence of three dimensional images from a specific viewing angle $\theta$ which are temporally sequential at closely spaced heart phases so as to show the real time motion of the heart in three dimensions over part or all of a heart cycle. Each time the user selects a different viewing angle $\theta$ the loop for that viewing angle is selected and displayed. For a smoothly transitioning image, the change from one viewing angle to the next will stop the first loop at a given temporal phase, then begin the succeeding loop at the same temporal phase from which the first loop was interrupted. The user can thereby view the beating heart from one viewing angle, then change the viewing angle to observe the beating heart from a different viewing angle. By continually changing the viewing angle the clinician is presented an appreciation of the beating heart from both spatial and temporal perspectives, and can fully examine the dynamics of the heart in motion.

It will be appreciated that the transfer function outputs of FIGS. 6 and 7 which are used to identify power Doppler signals from moving tissue can be inverted and applied to a gate circuit which passes only power Doppler signals from blood flow. Thus, the scan converter and display processor 34 and the image sequence memory 36 can simultaneously acquire and store separate, spatially discrete power Doppler images of both blood flow and tissue. These image sets can both be three dimensionally processed as described above to provide three dimensional images of both the heart and its blood pool. The two images can be separately color coded and viewed together, enabling the user to view both the heart chamber and its internal blood pool in two colors and three dimensions. The moving tissue of the heart muscle could be mapped in blue, for instance, and the blood pool mapped in red. It is possible of course to inhibit either color map and view either the blood pool or the heart wall alone in three dimensions.

It will also be appreciated that the idealized curves of FIGS. 6 and 7 can be varied from those shown in the drawings. The curves, and hence the response characteristics of the decision processors, can be modified so as to exhibit more curved or complex forms than the illustrated linear segments.

What is claimed is:

1. A method for producing three dimensional ultrasonic images of a moving organ or tissue within the body comprising the steps of:

transmitting ultrasonic waves over a volumetric region of the interior of the body containing an organ or tissue which is to be imaged;

receiving ultrasonic Doppler information signals from spatial locations within said organ or tissue;

processing said ultrasonic Doppler information signals to determine the Doppler power intensity received from said locations within said organ or tissue where tissue is in motion; and displaying the Doppler power intensity received from said organ or tissue motion on a spatial basis in a three dimensional presentation.

2. The method of claim 1, wherein the step of receiving comprises receiving ultrasonic Doppler information signals at a predetermined time of the cyclic motion of said organ or tissue.

3. The method of claim 2, wherein the step of displaying comprises presenting a three dimensional presentation of said organ or tissue motion representing the orientation of said organ or tissue motion at said predetermined time of the cyclic motion of said organ or tissue.

4. A method for producing ultrasonic images of a moving organ or tissue within the body comprising the steps of:

transmitting ultrasonic waves over a volumetric region of the interior of the body containing an organ or tissue which is to be imaged;

receiving ultrasonic Doppler information signals from spatial locations within said organ or tissue;

processing said ultrasonic Doppler information signals with a multivariate process to determine the Doppler power intensity received from said locations within said organ or tissue where tissue is in motion; and displaying the Doppler power intensity received from said organ or tissue motion on a spatial basis.

5. The method of claim 4, wherein the processing step comprises processing said ultrasonic Doppler information by considering Doppler power and velocity to determine the Doppler power intensity received from said locations within said organ or tissue where tissue is in motion.

6. An ultrasonic imaging system for producing ultrasonic images of a moving organ or tissue within the body comprising:

a multielement ultrasonic transducer which receives ultrasonic signals from said organ or tissue;

a beamformer, coupled to said transducer, for processing said ultrasonic signals to produce beams of ultrasonic information;

a Doppler processor responsive to said ultrasonic information for producing Doppler power signals corresponding to spatial locations within said organ or tissue;

a multivariate processor, responsive to said Doppler power signals, for discriminating Doppler power signals corresponding to moving tissue from Doppler power signals corresponding to fluid flow; and a display for displaying Doppler power information corresponding to tissue motion on a spatial basis.

7. The ultrasonic imaging system of claim 6, wherein said multivariate processor comprises:

a first discriminator responsive to said Doppler power signals for discriminating said Doppler power signals as a function of signal amplitude;

a second discriminator responsive to said Doppler power signals for discriminating said Doppler power signals as a function of frequency; and a decision circuit, responsive to said first and second discriminators, for identifying Doppler power signals corresponding to tissue motion.

8. The ultrasonic imaging system of claim 7, further comprising a user controlled threshold, coupled to said multivariate processor, for influencing the identification of Doppler power signals corresponding to tissue motion.

9. The ultrasonic imaging system of claim 8, wherein said user controlled threshold is coupled to said first or second discriminators.

10. The ultrasonic imaging system of claim 9, wherein said user controlled threshold comprises an amplitude threshold coupled to said first discriminator and a frequency threshold coupled to said second discriminator.

11. The ultrasonic imaging system of claim 10, wherein said decision circuit comprises a gate circuit, responsive to said discriminators, for passing Doppler power signals identified as corresponding to tissue motion.

12. The ultrasonic imaging system of claim 8, wherein said decision circuit comprises a gate circuit, responsive to said discriminators, for passing Doppler power signals identified as corresponding to tissue motion.

13. The ultrasonic imaging system of claim 7, wherein said first discriminator further comprises means for weighting said Doppler power signals as a function of signal amplitude, and wherein said second discriminator further comprises means for weighting said Doppler power signals as a function of frequency.

14. The ultrasonic imaging system of claim 13, wherein said first discriminator further comprises means for producing a first weighting coefficient which is a function of the amplitude of Doppler power signals, and wherein said second discriminator further comprises means for producing a second weighting coefficient which is a function of Doppler power signal frequency, wherein said displayed Doppler power information is a function of said first and second weighting coefficients.

15. The ultrasonic imaging system of claim 6, further comprising an image processor, responsive to Doppler power signals corresponding to moving tissue and coupled to said display, for processing Doppler power signals corresponding to tissue motion for display on a spatial basis in a three dimensional presentation.

16. The ultrasonic imaging system of claim 6, wherein said multivariate processor further comprises means for weighting said Doppler power signals as a function of their amplitude and frequency.

17. The ultrasonic imaging system of claim 6, further comprising means for processing Doppler power signals corresponding to moving tissue for display in a first color or range of colors; and means for processing Doppler power signals corresponding to fluid for display in a second color or range of colors.

18. The ultrasonic imaging system of claim 17, further comprising means for processing said colored moving tissue and fluid Doppler power signals for display on a spatial basis in a three dimensional presentation.

* * * * *